(12) United States Patent
Patil et al.

(10) Patent No.: US 11,039,793 B2
(45) Date of Patent: Jun. 22, 2021

(54) METHOD AND APPARATUS FOR CALIBRATING A MEDICAL MONITORING DEVICE

(71) Applicant: KONINKLIJKE PHILIPS N.V., Eindhoven (NL)

(72) Inventors: Meru Adagouda Patil, Bangalore (IN); Nagaraju Bussa, Bangalore (IN); Prasad Raghotham Venkat, Bangalore (IN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 313 days.

(21) Appl. No.: 16/061,925

(22) PCT Filed: Dec. 8, 2016

(86) PCT No.: PCT/EP2016/080160
§ 371 (c)(1),
(2) Date: Jun. 13, 2018

(87) PCT Pub. No.: WO2017/102521
PCT Pub. Date: Jun. 22, 2017

(65) Prior Publication Data
US 2018/0368779 A1      Dec. 27, 2018

(30) Foreign Application Priority Data
Dec. 15, 2015   (IN) .......................... 6716/CHE/2015

(51) Int. Cl.
*A61B 5/00*         (2006.01)
*A61B 5/1495*      (2006.01)
(Continued)

(52) U.S. Cl.
CPC .......... *A61B 5/7246* (2013.01); *A61B 5/1495* (2013.01); *A61B 5/327* (2021.01);
(Continued)

(58) Field of Classification Search
CPC ... A61B 5/6801; A61B 5/6803; A61B 5/7221; A61B 5/14532; A61B 5/168; A61B 5/7246
See application file for complete search history.

(56) References Cited

U.S. PATENT DOCUMENTS 6,309,884 B1 * 10/2001 Cooper .............. A61B 5/14532
356/39
2005/0197803 A1    9/2005 Eryurek et al.
(Continued)

FOREIGN PATENT DOCUMENTS

JP    2006138860 A    6/2006

OTHER PUBLICATIONS

Blumrosen et al: "New Wearable Body Sensor for Continuous Diagnosis of Internal Tissue Bleeding"; Conference Paper, 2009, 6 Page Document.
(Continued)

*Primary Examiner* — Regis J Betsch
*Assistant Examiner* — Kaleria Knox

(57) ABSTRACT

There is provided a method and apparatus for calibrating measurements made using a medical monitoring device. A conversion factor may be obtained including a first cross correlation that describes the correlation between measurements made using a first medical monitoring device and measurements made using a second medical monitoring device. The first conversion factor may then be used to convert measurements from the first medical monitoring device onto the same scale as measurements from the second medical monitoring device.

14 Claims, 7 Drawing Sheets

(51) Int. Cl.
  *A61B 5/327* (2021.01)
  *A61B 5/145* (2006.01)
  *A61B 5/1455* (2006.01)

(52) U.S. Cl.
  CPC ............ *A61B 5/681* (2013.01); *A61B 5/6802* (2013.01); *A61B 5/6898* (2013.01); *A61B 5/7221* (2013.01); *A61B 5/7278* (2013.01); *A61B 5/0006* (2013.01); *A61B 5/1455* (2013.01); *A61B 5/14532* (2013.01); *A61B 2560/0223* (2013.01)

(56) References Cited

U.S. PATENT DOCUMENTS

| | | | |
|---|---|---|---|
| 2008/0281220 A1 | 11/2008 | Sharifpour | |
| 2010/0081946 A1 | 4/2010 | Garudadri et al. | |
| 2012/0041279 A1* | 2/2012 | Freeman | A61M 5/168 |
| | | | 600/301 |
| 2013/0317332 A1* | 11/2013 | Feldman | A61B 5/7246 |
| | | | 600/365 |
| 2014/0051940 A1* | 2/2014 | Messerschmidt | A61B 5/6803 |
| | | | 600/301 |
| 2014/0236030 A1 | 8/2014 | Tan et al. | |
| 2015/0257689 A1* | 9/2015 | Al-Ali | A61B 5/6801 |
| | | | 702/104 |
| 2015/0289820 A1* | 10/2015 | Miller | A61B 5/7221 |
| | | | 600/300 |

OTHER PUBLICATIONS

Muaremi et al: "Towards Measuring Stress With Smartphones and Wearable Devices During Workday and Sleep"; BioNanoSci. (2013), vol. 3, pp. 172-183.

Fitbit:"Our Technology"; Fitbit Promotional Advertisement About Their Technology, CIO Magazine, Aug. 2016, 5 Page Document; Downloaded from the Internet at www.fitbit.com on Jun. 7, 2018.

NeuroSky: "Enabling Technologies for Next-Generation mHealth Solutions"; Promotional Advertisement for Biosensor Technologies, 2018, 2 Page Document, Downloaded from the Internet at http://store.neurosky.com/products/28-spoons, on Jun. 7, 2018, 3 Page Document.

The HeartCheck TM Advertisement for Handheld ECG Device for Self Monitoring, 6 Page Document, Downloaded from the Internet at http//www.theheartcheck.com, on Jun. 7, 2018.

* cited by examiner

METHOD AND APPARATUS FOR CALIBRATING A MEDICAL MONITORING DEVICE

CROSS-REFERENCE TO PRIOR APPLICATIONS

This application is the U.S. National Phase application under 35 U.S.C. § 371 of International Application No. PCT/EP2016/080160, filed on Dec. 8, 2016, which claims the benefit of India Patent Application No. 6716/CHE/2015 filed on Dec. 15, 2015. These applications are hereby incorporated by reference in their entirety herein.

TECHNICAL FIELD

Various embodiments described herein relate to the field of medical monitoring devices. More particularly, but not exclusively, various embodiments relate to methods of calibrating measurements made using a medical monitoring device.

BACKGROUND

Home based health monitoring devices are increasingly being used by the general public, both for monitoring known health conditions and more generally for health and fitness monitoring. Such monitoring devices may incorporate vital sign monitoring such as blood pressure (BP) monitoring and/or have the capability to track the progression of diseases. Portable ECG devices, for example, can be used to monitor heart disease. Some home based monitors are used for fitness regimes (for example, fitness bands/bracelets) and non-medical use cases like games consoles that are primarily used for gaming but incorporate vital sign monitors.

Although such devices help people to monitor their general health and changes in their health, the readings are not usually accurate enough to be directly used by clinicians to make clinical diagnoses or decisions. Clinicians are unable to use the outputs of such devices because the way the home based devices record patient parameters is different to the way that the same parameter is recorded in a clinical environment using a benchmark device. For example, home based BP monitors use automatic methods of detecting the systolic and diastolic beats that involve, for example, the detection of vibrations in the artery walls, whereas in a clinical setting the caregiver uses a stethoscope to listen for the systolic and diastolic beats. These different ways of measuring blood pressure can result in systematic differences between home based and clinical devices, and hence values from home based devices may not be suitable for clinical decision making.

SUMMARY

As noted above, the measurements from home based medical monitoring devices may be systematically offset to more traditional, clinically approved devices. In order to overcome these problems, it would be valuable to have an improved method and apparatus for calibrating a medical monitoring device.

Therefore, according to various embodiments, there is provided a method of calibrating measurements made using a medical monitoring device, the method including obtaining a first conversion factor including a first cross correlation that describes the correlation between measurements made using a first medical monitoring device and measurements made using a second medical monitoring device, and using the first conversion factor to convert measurements from the first medical monitoring device onto the same scale as measurements from the second medical monitoring device.

In some embodiments, the step of obtaining includes receiving a first set of measurements from the first medical monitoring device, receiving a second set of measurements from the second medical monitoring device, and computing the first cross correlation as the cross correlation between the first set of measurements and the second set of measurements;

In some embodiments, the step of obtaining further includes generating the first conversion factor from the first cross correlation by at least one of i) adding an offset to; and ii) scaling the first cross correlation using a scaling factor, wherein the offset and the scaling factor include one or more parameters relating to at least one of the first medical monitoring device and the second medical monitoring device.

In some embodiments, the one or more parameters relate to the degradation in performance over time of at least one of the first and the second medical monitoring device.

In some embodiments, the degradation in performance is described by an exponential term and the step of generating a first conversion factor includes adding the exponential term to the first cross correlation.

In some embodiments, the first conversion factor, C, is given by:

$$C = \sqrt{\frac{P_{xy}^2}{P_{xx}P_{yy}}} + e^{-\omega t};$$

wherein $P_{xy} = \Sigma xy - n\overline{x}\overline{y}$ represents the correlation between the measurements, x, from the first medical monitoring device and the measurements, y, from the second medical monitoring device; $P_{xx} = \Sigma(x_i - \overline{x})^2$ represents the auto-correlation of the measurements of the first medical monitoring device; $P_{yy} = \Sigma(y_i - \overline{y})^2$ represents the auto-correlation between the measurements from the second medical monitoring device; and $e^{-\omega t}$ represents the device performance degradation of the first medical monitoring device.

In some embodiments, the method further includes receiving a third set of measurements from the first medical monitoring device, receiving a fourth set of measurements from the second medical monitoring device, and updating the first conversion factor using the received third and fourth sets of measurements.

In some embodiments, the method further includes receiving a fifth set of measurements from the first medical monitoring device, receiving a sixth set of measurements from a third device, computing a second cross correlation between the fifth set of measurements and the sixth set of measurements, and generating a second conversion factor using the first and second cross correlations to convert measurements from the third device onto the same scale as measurements from the second medical monitoring device.

In some embodiments, the step of generating a second conversion factor includes calculating an intermediate conversion factor using the second cross correlation to convert measurements from the third device onto the same scale as the first medical monitoring device, and multiplying the intermediate conversion factor by the first conversion factor to obtain the second conversion factor.

In some embodiments, the step of using the first conversion factor includes: obtaining a calibration factor for the user, wherein the calibration factor indicates whether the physiological measurement should be divided or multiplied by the conversion factor; and dividing the physiological measurement by the conversion factor if the calibration factor indicates that the physiological measurement should be divided by the conversion factor, and multiplying the physiological measurement by the conversion factor if the calibration factor indicates that the physiological measurement should be multiplied by the conversion factor.

In some embodiments, the calibration factor is given by:

factor=1×sign($\Sigma(x-y)$)), where x and y are pairs of contemporaneous measurements of the first and second devices respectively.

In some embodiments the first and second sets of measurements are taken contemporaneously.

In some embodiments the first medical monitoring device is a home-based medical monitoring device and the second medical monitoring device is a clinical device.

According to some embodiments, there is a medical monitoring device comprising a computer processor configured to execute a method according to any of the methods above.

According to a some embodiments, there is a method of calibrating a physiological measurement of a user taken using a medical monitoring device, the method including: obtaining one or more characteristics relating to at least one of the device and the user; identifying the user from a plurality of users of the device using the one or more characteristics and a pattern based model; obtaining a conversion factor for the identified user using the device, to calibrate the physiological measurement; and calibrating the physiological measurement, using the conversion factor.

In some embodiments, the method further includes: obtaining a calibration factor for the user wherein the calibration factor indicates whether the physiological measurement should be divided or multiplied by the conversion factor; wherein the step of calibrating includes: dividing the physiological measurement by the conversion factor if the calibration factor indicates that the physiological measurement should be divided by the conversion factor; and multiplying the physiological measurement by the conversion factor if the calibration factor indicates that the physiological measurement should be multiplied by the conversion factor.

According to some embodiments, there is a method of associating a physiological measurement made on a medical monitoring device to a particular one of a plurality of users of the device, the method including: receiving training data including a set of measurements made using the device, wherein the training data further includes one or more parameters associating each measurement in the set of measurements with a user of the device; generating a model using the training data, wherein the model can be used to identify a user from a measurement made on the device; and associating a new measurement made on the device to a particular user of the device, using the model.

In some embodiments the model is a pattern based model or a linear predictor model.

In some embodiments the one or more parameters relate to one or more properties of the device or one or more user characteristics.

In some embodiments the one or more parameters includes at least one of an identification number, a device model, a tolerance limit, an accuracy, a performance, a performance degradation of the device, a time taken by the user to generate a measurement, the power needed to generate the measurement and the number of trials in the training data set.

In some embodiments the physiological measurement is a blood pressure measurement, the medical monitoring device is a blood pressure monitor and the linear predictor model is given by:

$$P_k = \beta_{0,k} + \beta_{1,k} D_{i,d} + \beta_{2,k} R_t + \beta_{3,k} P + \beta_{4,k} I_t + \beta_{5,k} D_t + \beta_{6,k} N$$

wherein $P_k$ is a patient identification number for the kth patient, $\beta_{0,k}$ is a constant coefficient, $\beta_{1,k}$ to $\beta_{6,k}$ are constant coefficients associated with corresponding parameters, $D_{i,d}$ is the device identification number, $R_t$ is the overall time taken by the patient to measure the blood pressure, P is the power needed to generate the pressure to take the measurement, $I_t$ is the time taken to inflate the calf wrapper, $D_t$ is the time taken to deflate the calf wrapper and N is the number of repeat trials.

According to some embodiments, there is provided a computer program product including a computer readable medium, the computer readable medium having computer readable code embodied therein, the computer readable code being configured such that, on execution by a suitable computer or processor, the computer or processor is caused to perform any one of the methods described above.

BRIEF DESCRIPTION OF THE DRAWINGS

For a better understanding, and to show more clearly how it may be carried into effect, reference will now be made, by way of example only, to the accompanying drawings, in which.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

To address the differences between home and clinical devices, patients may add or subtract certain values from the readings of the home based devices. However this method of calibration on its own may not be reliable enough for every patient and every device. Furthermore, this conversion is cumbersome for the patient, particularly if the patient data is provided in a stream of data, rather than discrete values. The accuracy of the home based device may also change (e.g. deteriorate) over time or if the patient changes their home-based device without reporting the change to their clinician, as the old offset value may not apply to the new device.

According to the foregoing, it would be desirable to provide an improved calibration method with increased reliability. It would also be desirable to provide such a calibration method that adapted to changing device conditions such as deterioration of the accuracy of the device or device swapping.

As noted above, various embodiments provide an improved method for calibrating a medical monitoring device.

Figure 1:
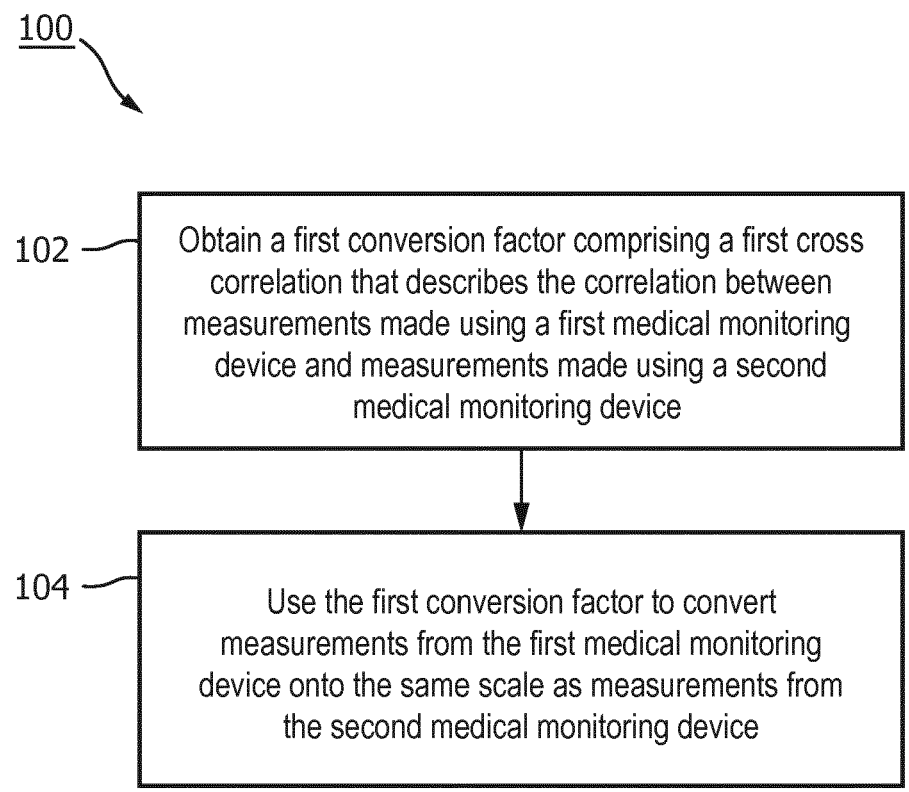
FIG. 1 is a block diagram illustrating an example of a method of calibrating measurements made using a medical monitoring device according to an embodiment.

FIG. 1 illustrates a method 100 of calibrating measurements made using a medical monitoring device. At block 102 the method includes obtaining a first conversion factor including a first cross correlation that describes the correlation between measurements made using a first medical monitoring device and measurements made using a second medical monitoring device. At block 104, the method then includes using the first conversion factor to convert measurements from the first medical monitoring device onto the same scale as measurements from the second medical monitoring device.

The use of a conversion factor including a cross correlation between measurements made using the device to be calibrated and a second medical monitoring device is an efficient and reliable way to produce a customised calibration for a medical monitoring device such as a home-based medical monitoring device. In particular, the cross correlation provides a statistical measure of how measurements of the first and second devices are related to one another. Using a data-driven approach in this way improves the accuracy of the calibration.

In some embodiments, the first medical monitoring device is a home based medical monitoring device, for example, a blood pressure monitor or portable ECG device. The first medical monitoring device may also be a home based device with sensors suitable for monitoring physiological characteristics of a user or patient, for example a fitness band, fitness bracelet or a games console that gathers physiological data that may otherwise be used, for example, in gaming. The first device may be capable of continuously monitoring one or more physiological characteristics of the user and producing a continuous stream of data values. The readings from the first medical monitoring device may generally need to be calibrated before they can be used by a clinician to make clinical diagnoses and decisions.

The first medical monitoring device can be used to monitor any physiological characteristic of the user, such as the blood pressure, muscle electrical activity (EMG), brain activity (EEG), heart rate or blood glucose levels of the user.

In some embodiments, the second device is a clinical device or 'bench mark' device, for example, a blood pressure monitor or ECG device found in a hospital. Measurements made using the second medical monitoring device may be used by a clinician to make clinical diagnoses or clinical decisions. It would thus be beneficial to calibrate the first medical monitoring device onto the same scale as the second medical monitoring device.

As described above, the conversion factor may include a first cross correlation that describes the cross correlation between measurements made using the first medical monitoring device and measurements made using the second medical monitoring device. The step of obtaining 102 may therefore include calculating the cross correlation by receiving a first set of measurements from the first medical monitoring device, receiving a second set of measurements from the second medical monitoring device and computing the first cross correlation as the cross correlation between the first set of measurements and the second set of measurements The first set of measurements and the second set of measurements may have been taken contemporaneously, e.g. at approximately the same time. In this context, contemporaneously can mean that the first and second sets of measurements are taken within a time interval over which the physiological characteristic measured by the first medical monitoring device is approximately constant (or does not significantly change between measurements). For example, a clinician may make one or more measurements of a user's blood pressure on a clinical device at the same time as a wrist worn home based device takes measurements of the user's blood pressure. This has the advantage of taking care of temporal variation in the parameter to ensure that the first set of measurements and the second set of measurements are comparable and can be reliably used to calibrate the first medical monitoring device without having to take account of changes in the value of the physiological parameter between when the first set of measurements were taken and the second set of measurements were taken.

In some embodiments, the first cross correlation, r, may be calculated from the first set of measurements and the second set of measurements according to the following equation:

$$r = \sqrt{\frac{P_{xy}^2}{P_{xx}P_{yy}}}$$

Where x represents measurements from the first medical monitoring device, y represents measurements from the second medical monitoring device, $P_{xy}=\Sigma xy-n\overline{x}\overline{y}$ represents the correlation between the measurements, x and y; $P_{xx}=\Sigma(x_i-\overline{x})^2$ represents the auto-correlation of the measurements of the first medical monitoring device; and $P_{yy}=\Sigma(y_i-\overline{y})^2$ represents the auto-correlation between the measurements from the second medical monitoring device.

In some embodiments, the first conversion factor is equal to the first cross correlation, r. In other embodiments, the first conversion factor is generated from the first cross correlation by at least one of adding an offset to the cross correlation and scaling the first cross correlation using a scaling factor. The offset or scaling factor may relate to a characteristic of at least one of the first medical monitoring device and the second medical monitoring device, such as the degradation in performance over time of the first medical monitoring device or the second medical monitoring device.

For example, if it is known that the first medical monitoring device systematically underestimates the measured physiological parameter and that this underestimation becomes more pronounced by a factor of d, every month, then the first conversion factor, C, may be generated from the first cross correlation according to $C=r/d^m$ where m is the number of months since the first set of measurements and the second set of measurements were made.

In another example, the degradation in performance may be described by an exponential term and the step of generating a first conversion factor may include adding the exponential term to the first cross correlation. The first conversion factor, C, may therefore be given by:

$$C = \sqrt{\frac{P_{xy}^2}{P_{xx}P_{yy}}} + e^{-\omega t};$$

where $P_{xy} = \Sigma xy - n\overline{xy}$ represents the correlation between the measurements, x, from the first medical monitoring device and the measurements, y, from the second medical monitoring device; $P_{xx} = \Sigma(x_i - \overline{x})^2$ represents the auto-correlation of the measurements of the first medical monitoring device; $P_{yy} = \Sigma(y_i - \overline{y})^2$ represents the auto-correlation between the measurements from the second medical monitoring device; and $e^{-\omega t}$ represents the device performance degradation of the first medical monitoring device. In this way, the first device can be reliably calibrated over its lifetime, even if it degrades in performance.

In some embodiments, in block 102, obtaining a first conversion factor includes obtaining the first conversion factor from computer storage, for example from a memory module, a network location or a database.

In other embodiments, block 102 includes generating the first conversion factor, for example, calculating the cross correlation as described above, calculating the cross correlation and then scaling and/or adding an offset to the cross correlation, or generating the first conversion factor from a pre-computed cross-correlation and scaling and/or adding an offset to the precomputed cross correlation. The first conversion factor can therefore be stored as a single value for use in calibration, or alternatively, the first cross correlation can be stored separately from the offset and/or scaling factor and combined to form the first conversion factor at run-time. Alternatively still, one or both of the first conversion factor and the offset and or scaling factor can be calculated or updated at run time. This is particularly relevant if the offset or scaling factor relate to one or more parameters that are received from the first or second medical monitoring devices in real time.

Generation of the first conversion factor may also occur when the user first starts to use the first medical monitoring device, when the user initiates a calibration routine on the first medical monitoring device, at regular intervals (for example, the conversion factor may be periodically updated) or the first conversion factor may be generated in real time and recomputed every time that a measurement made using the first medical monitoring device needs to be calibrated.

The conversion factor may be updated using additional measurements from the first and second medical monitoring devices. For example, in some embodiments, the method may include receiving a third set of measurements from the first medical monitoring device, receiving a fourth set of measurements from the second medical monitoring device and updating the first conversion factor using the received third and fourth sets of measurements.

The third and fourth sets of measurements (or any subsequent sets of measurements) may be taken when the user is in a clinical setting, for example when the user visits the doctor's surgery or hospital. In this way, the third and fourth sets of measurements can be taken contemporaneously (e.g. at approximately the same time, or over a time scale over which the physiological parameter being measured does not significantly change) so that the measurements can be used for calibration without having to take account of any change of the physiological parameter between the third and fourth sets of measurements. The first conversion factor can thus be periodically updated when the user visits a clinical setting.

The step of using the first conversion factor 104 may include multiplying or dividing measurements made using the first medical monitoring device by the first conversion factor. In some embodiments, using the first conversion factor may include receiving a calibration factor that indicates whether the measurements made using the first medical monitoring device should be multiplied or divided by the first conversion factor in order to be calibrated onto the same scale as measurements made using the second device. The calibration factor can be an integer, for example, the calibration factor may be denoted by either +1 or −1, where +1 indicates that the measurements should be multiplied by the first conversion factor and −1 indicates that the measurements should be divided by the first conversion factor.

In some embodiments, the calibration factor is given by:

factor=1×sign(Σ(x−y)), where x and y are pairs of contemporaneous measurements of the first and second devices respectively and sign represents the sign or signum function that extracts the sign (e.g. + or −) of its operand.

These calculations are illustrated in the following example, where Table 1 shows a list of blood pressure measurements made using clinical and home-based blood pressure monitoring devices. Each row of measurements in Table 1 were made contemporaneously, e.g. approximately the same time, such that the underlying blood pressure does not significantly change between readings. Differences between the clinical and home based readings therefore reflect an offset between the devices rather than differences in the underlying blood pressure being measured.

TABLE 1

| Clinical Device Readings | | Home Device Readings | |
| --- | --- | --- | --- |
| Systolic | Diastolic | Systolic | Diastolic |
| 102 | 65 | 106 | 60 |
| 100 | 61 | 102 | 54 |
| 120 | 83 | 121 | 79 |
| 122 | 83 | 125 | 79 |
| 124 | 85 | 127 | 79 |
| 113 | 78 | 114 | 76 |
| 116 | 79 | 119 | 75 |
| 114 | 79 | 116 | 72 |
| 115 | 79 | 117 | 74 |
| 124 | 87 | 127 | 81 |
| 122 | 87 | 124 | 81 |
| 121 | 86 | 123 | 81 |
| 124 | 89 | 128 | 87 |
| 120 | 81 | 122 | 76 |
| 116 | 81 | 121 | 80 |

Using the equations given above, the cross correlation, r, is equal to 0.9889 and 0.9784 for the systolic and diastolic blood pressure measurements respectively and the calibration factors are 1 and −1 respectively. Considering an example where the conversion factors are equal to the cross correlation values, the conversion factors to convert the systolic and diastolic measurements made using the home based device onto the same scale as the clinical device are also 0.9889 and 0.9784 respectively.

The calibration factors indicate that in this case, the systolic blood pressure measurements made using the home based device need to be multiplied by the systolic conversion factor (0.9889) in order to convert them onto the same scale as the clinical device. Conversely, the diastolic measurements from the home based device need to be divided by the conversion factor for diastolic measurements (0.9784) in order to convert them onto the same scale as the diastolic clinical measurements.

In this example, if the home based monitoring device were to make a blood pressure measurement of 115/75, then using the conversion factors and calibration factors given above, this would be equal to 114/77 when scaled onto the same scale as the clinical device.

In a second example, if the home based device is known to degrade according to the data in Table 2 below, then after 6 months, the Conversion Factor can be calculated according to $$C = \sqrt{\frac{P_{xy}^2}{P_{xx}P_{yy}}} + e^{-\omega t}$$

as described above, where $$\sqrt{\frac{P_{xy}^2}{P_{xx}P_{yy}}}$$

is the cross correlation between the home based medical monitoring device and the clinical medical monitoring device as calculated in example 1 above and $e^{-\omega t}$ represents the device performance degradation of the home based medical monitoring device.

TABLE 2

| Age of device (months) | Performance degradation (%) |
|---|---|
| 1 | 0 |
| 2 | 0.5 |
| 3 | 0.6 |
| 4 | 1.0 |
| 5 | 2.0 |
| 6 | 2.5 |

In this case, after 6 months, the conversion factors for the systolic and diastolic measurements are now 0.9891 and 0.9782 respectively. The calibration factors are still 1 and −1 respectively. If after 6 months, the home device were to make a blood pressure measurement of 116/76, then using the conversion factors and calibration factors above, this would then be converted to 114/77 on the scale of the clinical medical monitoring device.

Figure 2:
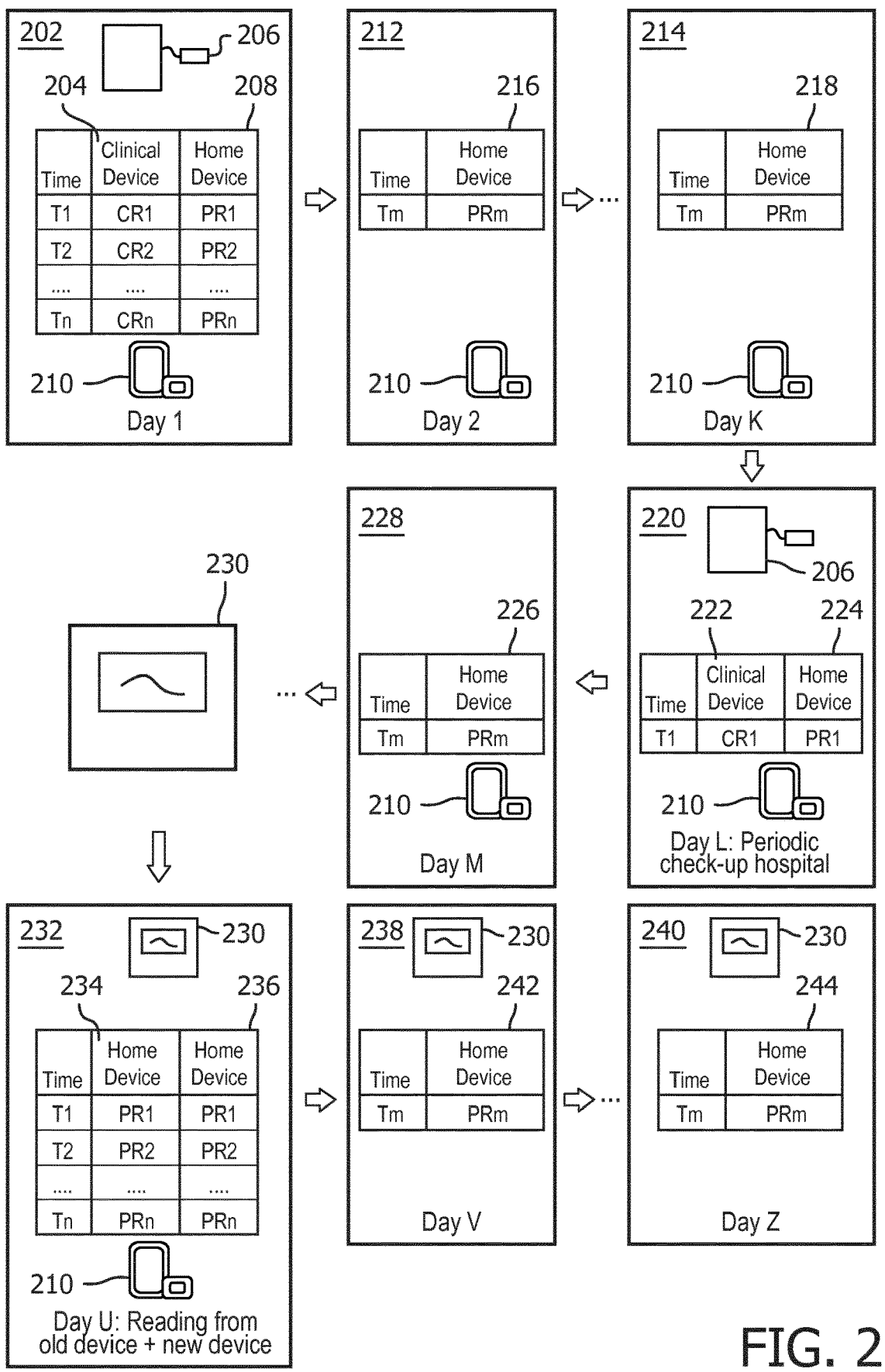
FIG. 2 is a schematic of an example of a method of calibrating a medical monitoring device according to another embodiment.

FIG. 2 illustrates an embodiment of the method of calibrating a device as described above. In box 202, the user visits a clinical setting where a clinician such as a doctor or nurse takes a set of clinical measurements 204 of a physiological parameter using a clinical device 206. The set of clinical measurements are suitable to be used to make clinical decisions or diagnoses. In the context of the description above, the clinical device is the second medical monitoring device and the set of clinical measurements is the second set of measurements.

Whilst the set of clinical measurements are being made, a set of home-based measurements 208 of the same parameter are also made using a home based device 210, such as a home based blood pressure monitor, ECG, fitness bracelet or games console. In the context of the discussion above, this set of measurements is the first set of measurements and the home-based device 210 is the first medical monitoring device. The set of measurements made by the home based device are referred to as the set of home based measurements in this example. The set of home based measurements are made contemporaneously e.g. substantially at the same time as the set of clinical measurements, as described in detail above.

A first cross correlation and first conversion factor are then calculated from the set of clinical measurements 204 and the set of home based measurements 208. In boxes 212 and 214, measurements 216, 218 made on the home based device 210 at a later time (for example a time when the user is at home or not in a clinical setting) can then be calibrated onto the same scale as measurements from the clinical device 206, using the first conversion factor.

If at some later date in box 220, the user returns to the clinical setting, a fourth set of measurements 222 of the same physiological parameter can be made using the clinical device, contemporaneously, or substantially at the same time as a third set of measurements 224 are made using the home based device 210. The third and fourth sets of measurements 222, 224 can then be used to update the first cross correlation and the first conversion factor. Subsequent measurements 226 made using the home based device 210 at a later time 228 can then be calibrated using the updated cross correlation and updated first conversion factor.

If, after some time, the user decides to buy a new home based device 230, to replace the original home based device 210, the new home based device 230 can be calibrated (box 232) onto the clinical device by first calibrating the new home based device 230 onto same scale as the original home based device 210 and then using the known first conversion factor to calibrate the measurements from the scale of the original home based device to the scale of the clinical device. In this way the new home based device 230 can be calibrated onto the clinical device 206 via the old home based device 210, without the need for the user to revisit the clinical setting.

This can be achieved by taking a fifth set of measurements 234 using the original home based device 210 and a sixth set of measurements 236 from the new home based device 230 and computing a second cross correlation between the fifth set of measurements 234 and the sixth set of measurements 236. A second conversion factor can then be generated using the first and second cross correlations to convert measurements from the new home based device 230 onto the same scale as measurements from the clinical device 206.

The second conversion factor can be generated by calculating an intermediate conversion factor using the second cross correlation that converts measurements from the third device onto the same scale as the first medical monitoring device, and then multiplying the intermediate conversion factor by the first conversion factor to obtain the second conversion factor.

At later times 238, 240, measurements 242, 244 made using the new home based device 230 can be calibrated onto the same scale as the clinical device 206, using the second conversion factor. Calibrating a new home based device onto a clinical device via an old home based device in this way has the advantage of enabling the user to calibrate the new home based device to clinical standards without the user having to visit a clinician to obtain new clinical measurements.

Calibrating home based devices using the methods provided above provides opportunities for continuous clinical monitoring of patients using measurements from both traditional home-based medical monitoring devices such as blood pressure monitors and ECG monitors, but also from other devices such as fitness monitors and games consoles. Such measurements may be sent to a clinician for monitoring of an individual, or for statistical purposes, such as in population health studies where the health outcomes of groups of individuals are analysed.

In this context, it is important to be able to match otherwise anonymous health data and physiological measurements to an individual. It is also important to be able to match physiological measurements to a particular user in cases where more than one user uses a device.

Figure 3:
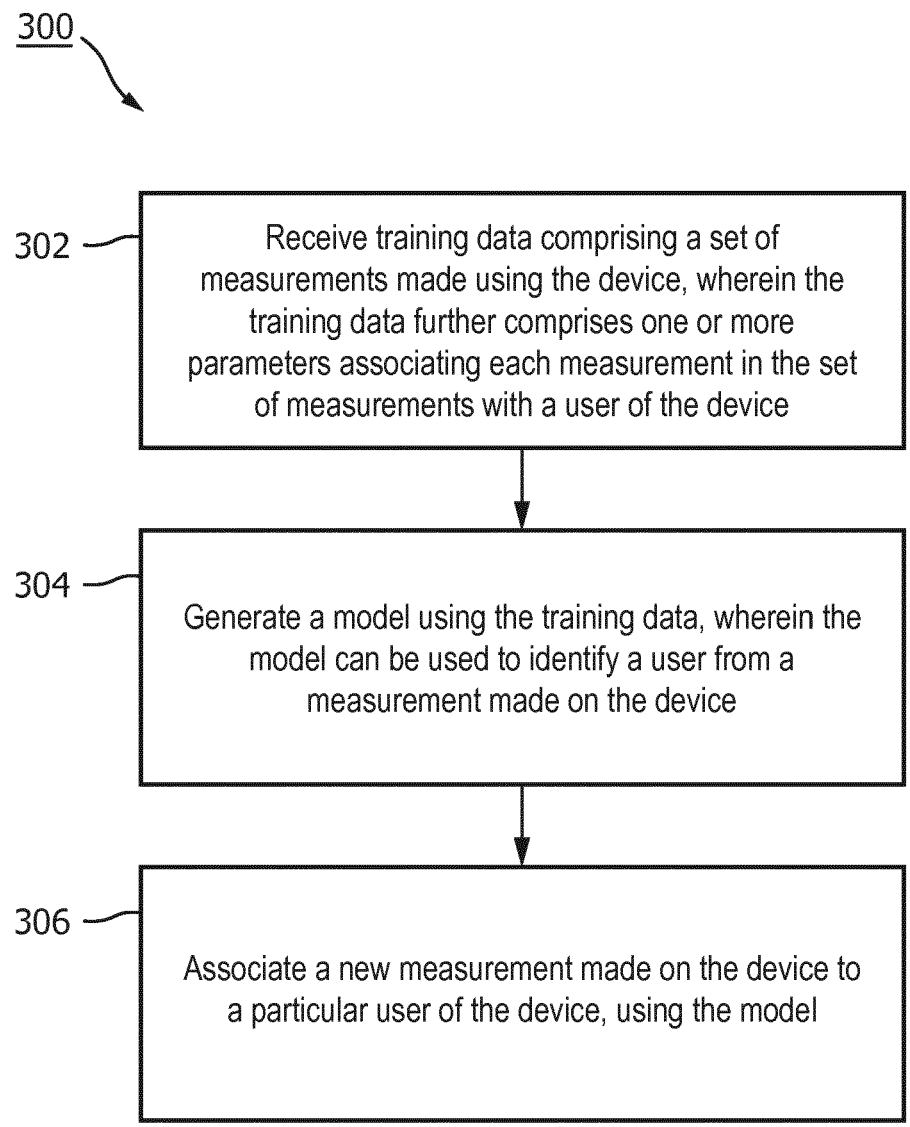
FIG. 3 is a block diagram showing an example of a method of associating a physiological measurement made on a medical monitoring device to a particular one of a plurality of users of the device.

To this end, FIG. 3 shows a method 300 of associating a physiological measurement made on a medical monitoring device to a particular one of a plurality of users of the device. In block 302, the method includes receiving training data including a set of measurements made using the device, wherein the training data further includes one or more parameters associating each measurement in the set of measurements with a user of the device. In block 304 the model then includes generating a model using the training data, wherein the model can be used to identify a user from a measurement made on the device. In block 306 a new measurement made on the device is associated with a particular user of the device, using the model.

In some embodiments, the one or more parameters relate to one or more properties of the device, such as an identification number, a device model, a tolerance limit, an operating environment, an accuracy, a performance or a performance degradation of the device. The one or more parameters can also relate to one or more user characteristics such as a time taken by the user to generate a measurement, the power needed to generate the measurement, the number of trials in the training data set, the time of the day of recording a measurement, the number of recordings in a 24 hour period, or the actual values measured. In general, any parameter can be used, so long as it is able to distinguish between one or more user and device combinations.

In some embodiments, the model is a pattern based model or a linear predictor model. This may be represented by an equation such as:

$$P_k = \beta_{0,k} + \beta_{1,k} p_1 + \beta_{2,k} p_2 + \beta_{3,k} p_3 + \ldots + \beta_{N,k} p_n$$

where $P_k$ is a unique patient identification number for the kth patient using a particular device, $\beta_{0,k}$ is a constant coefficient and $\beta_{1,k}$ to $\beta_{N,k}$ are constant coefficients associated with the corresponding parameters $p_1$ to $p_n$. A patient may have more than one unique patient identification number if they use more than one device. Each patient identification number therefore identifies a user case of a particular user using a particular device.

The constant coefficients of the pattern based model can be generated using a machine learning algorithm. Examples of suitable machine learning algorithms include Support Vector Regression, Linear Regression and Radial Basis Function Regression. The number of parameters and the particular combination of parameters chosen for use in the model depends on the users and the particular devices in the training data set. In general, any number of parameters and any combination of parameters can be used so long as a weighted combination of the chosen parameters can be found that produces a unique value for each user. In this way, a patient can be identified using a weighted combination of parameter values associated with a physiological measurement.

Figure 4:
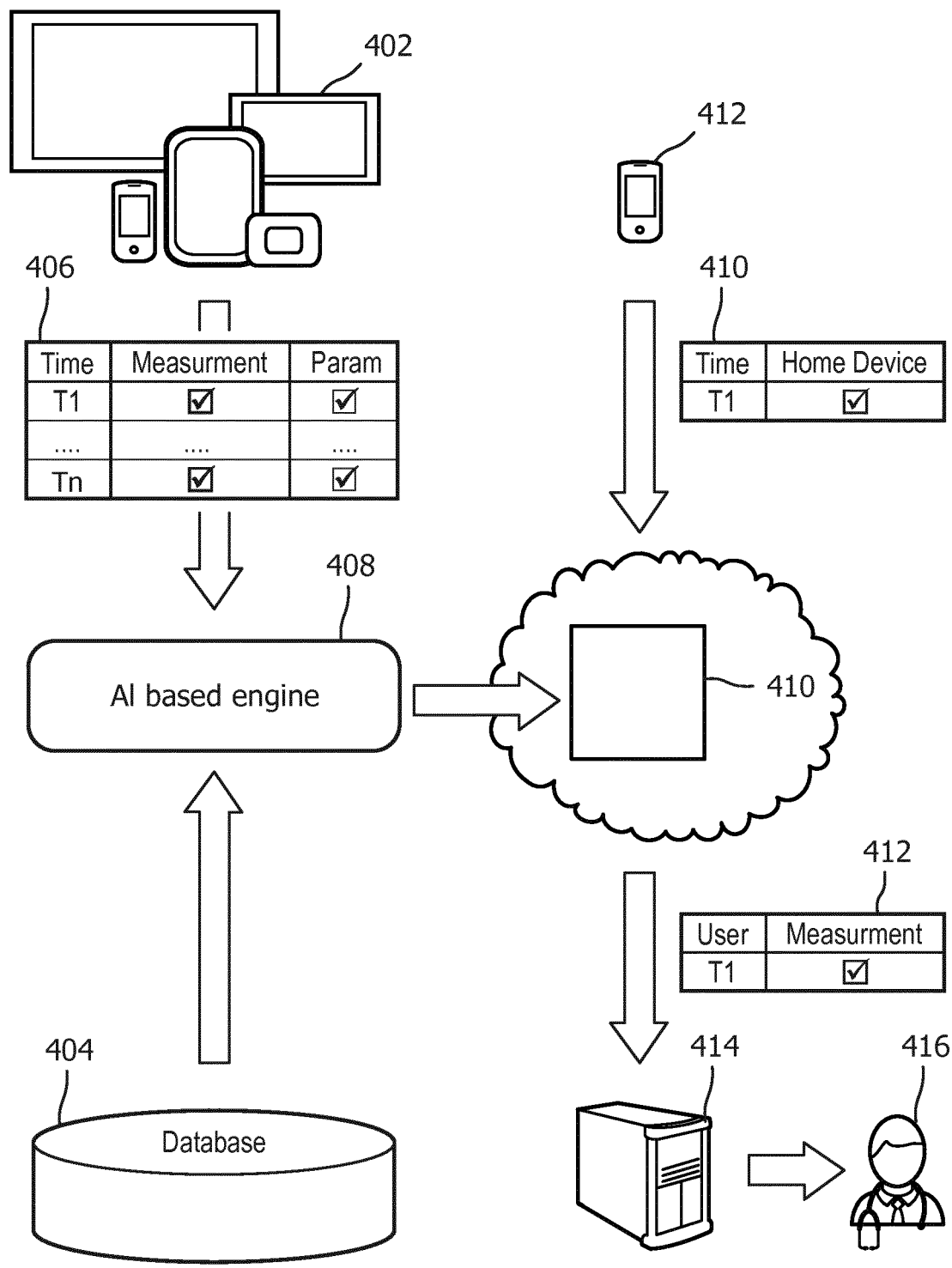
FIG. 4 is a schematic of an example of a method of calibrating a medical monitoring device according to an embodiment.

This method is illustrated further in FIG. 4 which shows a plurality of medical monitoring devices 402 and a database 404. The database 404 contains parameter values relating to the plurality of medical monitoring devices 402. The parameter values may be public information, such as device specification information, tolerance limits, operating environment information and device performance over time, or values previously received from the device. Measurements from the devices and parameter values 406 for each device are fed into an artificial intelligence (AI) engine 408. Artificial intelligence engine 408 generates a model 410 from the inputted data using a machine learning algorithm. As described above, the model may be a pattern based model or a linear predictor model that links certain parameters relating to the user, the measurement and/or a device to a specific user using a specific device.

The model 410 may be stored in the cloud, on a centralised server or on the devices themselves. Storing the model directly on the devices may be particularly relevant when trying to distinguish between different users of a device.

For each medical monitoring device of the plurality of medical monitoring devices, a conversion factor is obtained, using one of the methods described above, that can be used to convert measurements from said monitoring device onto the same scale as measurements from a clinical monitoring device. The conversion factor includes a cross correlation that describes the correlation between measurements made using said medical monitoring device and a clinical device. The conversion factor and cross correlation is obtained using any of the methods described above.

When a new measurement 410 is made using a device 412 which is one of the plurality of medical monitoring devices 402, the measurement and one or more parameters are then used to identify the associated user, using the one or more parameters and the model 410. Once the user is identified, a conversion factor can be retrieved for the identified user and device and the physiological measurement can be calibrated using the conversion factor. The user identity and the calibrated measurement 412 can then be sent to a clinic 414 for use by a clinician 416.

The method above can also be applied to anonymous data, in the sense that the patient ID does not have to be stored with or in any way associated with details that identify the associated individual (e.g. the individual's name or address). Individuals can thus be anonymously tracked over time just using a patient ID, the data for use, for example, in studies of population health.

Figure 5:
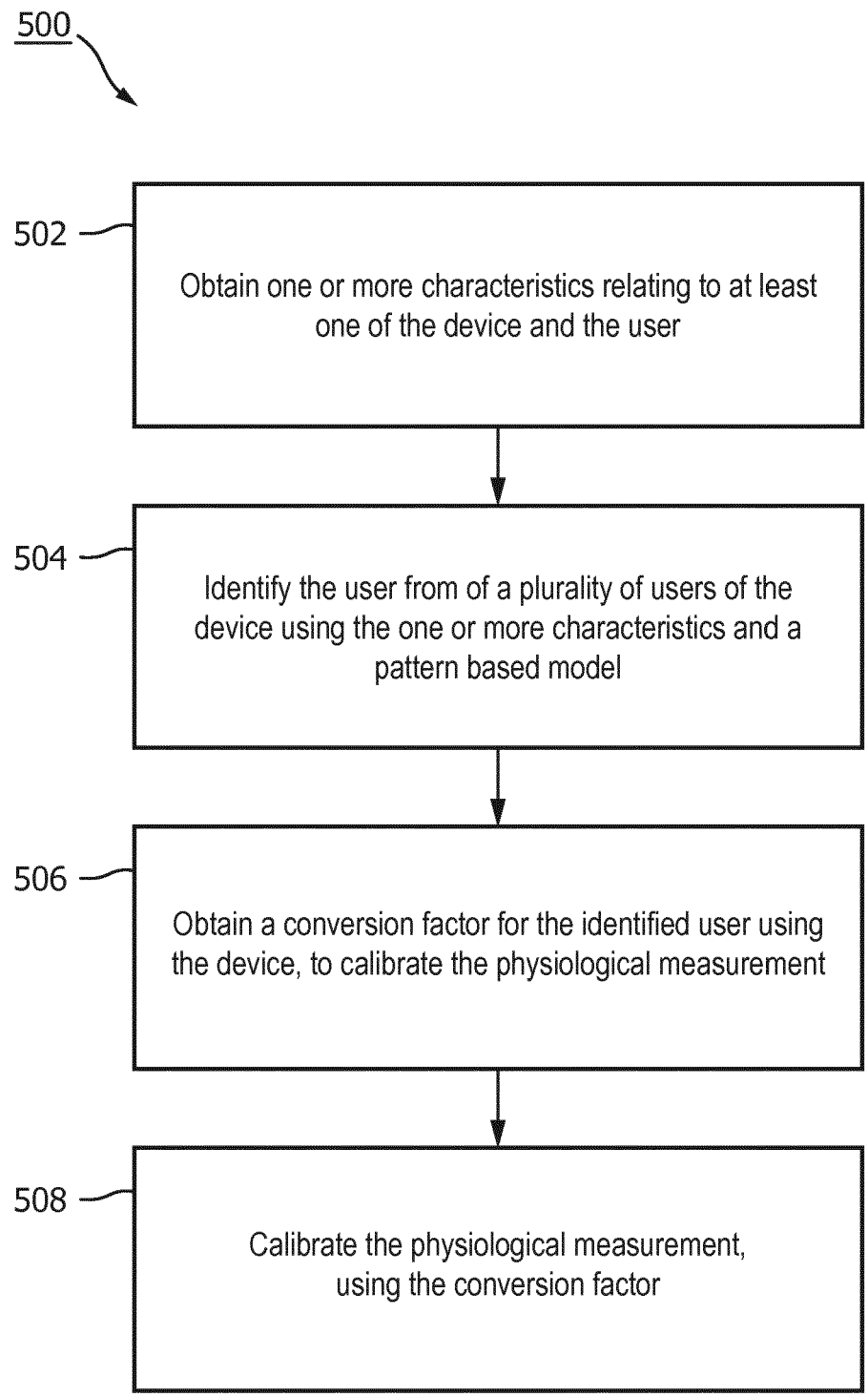
FIG. 5 is a block diagram of an example of a method of calibrating a medical monitoring device according to an embodiment.

A more general illustration of this method is shown in FIG. 5. In a first step 502, the method includes obtaining one or more characteristics relating to at least one of the device and the user. At 504 the method includes identifying the user from a plurality of users of the device using the one or more characteristics and a pattern based model. At 506, the method includes obtaining a conversion factor for the identified user using the device, to calibrate the physiological measurement, and at 508, the method includes calibrating the physiological measurement using the conversion factor.

As described above, the one or more characteristics can relate to one or more properties of the device, such as an identification number, a device model, a tolerance limit, an accuracy, a performance or a performance degradation of the device. The one or more parameters can also relate to one or more user characteristics such as a time taken by the user to generate a measurement, the power needed to generate the measurement, the number of trials in the training data set, the time of the day of recording a measurement, the number of recordings in a 24 hour period, or the actual values measured.

The precise number and combination of parameters used may vary and in general, any number and combination of parameters can be used so long as they can be combined in the pattern based model in such a way as to result in a unique value for each A further example of the preceding methods will now be given, where the first medical monitoring device is a home based blood pressure monitor and the second medical monitoring device is a clinical blood pressure monitor.

In this example, the first step is to collect patient blood pressure readings from both the clinical device (e.g. the second medical monitoring device) and home-based device (e.g. the first medical monitoring device) at time $T_1$. In step 2, an association is created between the time the measurements are taken and the systolic and diastolic home-based blood pressure device readings ($H_{SBP}*\alpha T_1$, $H_{DySBP}*\beta T_1$) to generate time independent values. $\alpha$ and $\beta$ are scaling parameters in these equations.

In step 3, the following relationships between the clinical measurements and the home device measurements are then made:

$$C_{SBP} \rightarrow H_{SBP}*\alpha T_1$$

$$C_{DySBP} \rightarrow H_{DySBP}*\beta T_1$$

where $C_{SBP}$ and $C_{DySBP}$ are the systolic and diastolic BP readings made using the clinical device made at T1, and $H_{SBP}$ and $H_{DySBP}$ are the systolic and diastolic BP readings using the home-based device at T1.

In step 4, the time is delayed by a time interval $T_x$

In step 5, the following additional parameters are also recorded: Device ID ($D_{ID}$), Time taken to measure BP by patient ($R_{Time}$), Power needed to generate calf pressure ($P_{need}$), Time taken to inflate calf wrapper ($Inf_{Time}$), Time taken to deflate calf wrapper ($Def_{Time}$) and the Number of repeat trials ($N_{Trial}$).

In step 6, the stages 1 to 4 are repeated until n samples are collected.

In step 7, home based device specification details are obtained, for example the device decalibration rate.

In step 8: A conversion factor for systolic BP is calculated using the equation:

$$C_{SBP} = \sqrt{\frac{SBP_{xy}^2}{SBP_{xx}SBP_{yy}}} + e^{-\omega t}$$

where $SBP_{xy}=\Sigma xy - n\overline{xy}$ represents the correlation between the clinical ($x=C_{SBP}$) and home-based time-independent ($y=H_{SBP}*\alpha T$) systolic BP readings;

$SBP_{xx}=\Sigma(x_i-\overline{x})^2$ represents auto-correction of clinical device systolic BP readings;

$SBP_{xx}=\Sigma(x_i-\overline{x})^2$ represents the auto-correction of time-independent home-based device systolic BP readings and $e^{-\omega t}$ represents the device de-calibration rate (device performance degradation rate). It is noted that the conversion factor for systolic blood pressure includes the cross correlation term $$\sqrt{\frac{SBP_{xy}^2}{SBP_{xx}SBP_{yy}}}.$$

In step 9: A conversion factor for diastolic BP is calculated according to:

$$C_{DySBP} = \sqrt{\frac{DySBP_{xy}^2}{DySBP_{xx}DySBP_{yy}}} + e^{-\omega t}$$

Where $DySBP_{xy}=\Sigma xy - n\overline{xy}$ represents the correlation between the clinical ($x=C_{DySBP}$) and Home-based time-independent ($y=H_{DySBP}*\beta T$) diastolic BP readings, $DySBP_{xx}=\Sigma(x_i-\overline{x})^2$ represents the auto-correction of clinical device diastolic BP readings, $SBP_{xx}=\Sigma(x_i-\overline{x})^2$ represents auto-correction of time-independent home-based device diastolic BP readings and $e^{-\omega t}$ Represents device de-calibration rate (device performance degradation rate). It is noted that the conversion factor for the diastolic blood pressure includes the cross correlation term $$\sqrt{\frac{DySBP_{xy}^2}{DySBP_{xx}DySBP_{yy}}}.$$

In step 10: both the systolic and diastolic conversion factors are stored on a server or in the cloud where they are associated with a unique patient ID and device ID.

In step 11: Steps 1-10 can be repeated, with additional data each time the user records additional measurements when the home-based and clinical device are together (e.g. when measurements can be made over a time period over which the physiological parameter does not significantly change) such as when the user visits their clinician or doctor.

In practice, the systolic and diastolic conversion factors can be used in conjunction with a patient identification module (in the case of connected Home device):

The patient identification module will be part of the complex logic that is responsible for matching the correct model with correct device and patient ID. This module will be needed in cases where device is directly connected to internet and data is pushed by device without patient identification information (as which patient has used the device) and/or when the device is shared by multiple users. The patient identification module is built using pattern recognition techniques as described below.

In Stage 1: The parameters recorded during training phase are associated with a patient ID. Example parameters are the Device ID ($D_{ID}$), Time taken to measure BP by patient ($R_{Time}$), Power needed to generate calf pressure ($P_{need}$), Time taken to inflate calf wrapper ($Inf_{Time}$), Time taken to deflate calf wrapper ($Def_{Time}$) and the Number of repeat trials ($N_{Trial}$).

In stage 2: A pattern-based AI model (e.g. a Linear Predictor model) is built that associates the patient ID with the parameters recorded during the training phase. The pattern based model is given by:

$$P_k = \beta_{0,k} + \beta_{1,k}D_{id} + \beta_{2,k}R_t + \beta_{3,k}P + \beta_{4,k}I_t + \beta_{5,k}D_t + \beta_{6,k}N$$

where:

$P_k$ is the patient ID for the kth patient $\beta_{0,k}$ Constant Coefficient. $\beta_{1,k}$ to $\beta_{6,k}$ are coefficients associated with the corresponding parameters $D_{id}$ Device ID $R_t$ Over all time taken by patient to measure BP P Power needed to generate calf pressure $I_t$ Time taken to inflate calf wrapper $D_t$ Time taken to deflate calf wrapper N Number of repeat trials In stage 3: The model is then stored and can be used as part of the complex logic to match unknown patient data to a particular patient and device.

Generally, the model can be enhanced by increasing the number of parameters, for example, the time of the day of recording measurements, the number of recordings in 24 hr and/or the actual values of the measurements can all be used in the model to discriminate between different patients.

Figure 6:
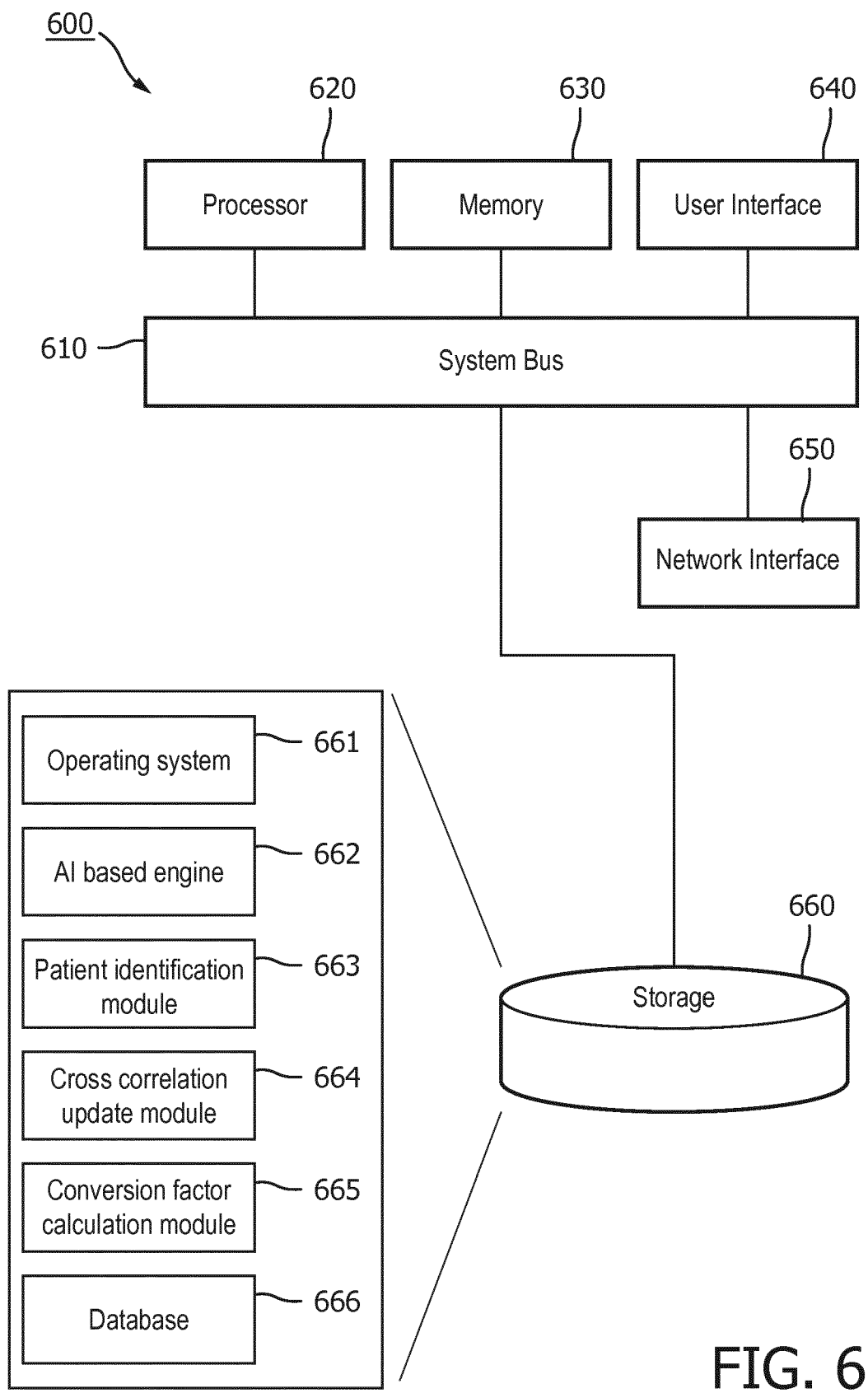
FIG. 6 is a schematic of an example apparatus for calibrating a medical monitoring device.

FIG. 6 illustrates an exemplary hardware diagram 600 of a device suitable for calibrating measurements made using a medical monitoring device. As shown, the device 600 includes a processor 620, memory 630, user interface 640, network interface 650, and storage 660 interconnected via one or more system buses 610. It will be understood that FIG. 6 constitutes, in some respects, an abstraction and that the actual organization of the components of the device 600 may be more complex than illustrated.

The processor 620 may be any hardware device capable of executing instructions stored in memory 630 or storage 660 or otherwise processing data. As such, the processor may include a microprocessor, field programmable gate array (FPGA), application-specific integrated circuit (ASIC), or other similar devices.

The memory 630 may include various memories such as, for example L1, L2, or L3 cache or system memory. As such, the memory 630 may include static random access memory (SRAM), dynamic RAM (DRAM), flash memory, read only memory (ROM), or other similar memory devices.

The user interface 640 may include one or more devices for enabling communication with a user such as an administrator. For example, the user interface 640 may include a display, a mouse, and a keyboard for receiving user commands. In some embodiments, the user interface 640 may include a command line interface or graphical user interface that may be presented to a remote terminal via the network interface 650.

The network interface 650 may include one or more devices for enabling communication with other hardware devices such as one or more medical monitoring devices. For example, the network interface 650 may include a network interface card (NIC) configured to communicate according to the Ethernet protocol. Additionally, the network interface 650 may implement a TCP/IP stack for communication according to the TCP/IP protocols. Various alternative or additional hardware or configurations for the network interface 650 will be apparent.

The storage 660 may include one or more machine-readable storage media such as read-only memory (ROM), random-access memory (RAM), magnetic disk storage media, optical storage media, flash-memory devices, or similar storage media. In various embodiments, the storage 660 may store instructions for execution by the processor 620 or data upon with the processor 620 may operate. For example, the storage 660 may store a base operating system 661 for controlling various basic operations of the hardware 600.

Storage 660 may also store instructions for an AI based engine 662 for generating a model that can be used to match a measurement made on a device to a user of the device. The model can be a pattern based model or a linear predictor model, as described above. Storage 660 may also store instructions for a patient identification module 663 that is configured to use models generated by AI based engine 662 to match data received from a home based monitoring device to an individual user. In addition the processor further includes instructions for a cross correlation update module 664 and a conversion factor calculation module 665 for calculating the cross correlation and conversion factors respectively between pairs of first and second devices, as described above.

Storage 660 can also include a database 666 that may store, amongst other things, measurements made by devices, parameters relating to said devices, cross correlations between medical monitoring devices, conversion factors between medical monitoring devices and models generated by the AI based engine 662.

It will be apparent that various information described as stored in the storage 660 may be additionally or alternatively stored in the memory 630. In this respect, the memory 630 may also be considered to constitute a "storage device" and the storage 660 may be considered a "memory." Various other arrangements will be apparent. Further, the memory 630 and storage 660 may both be considered to be "non-transitory machine-readable media." As used herein, the term "non-transitory" will be understood to exclude transitory signals but to include all forms of storage, including both volatile and non-volatile memories.

While the host device 600 is shown as including one of each described component, the various components may be duplicated in various embodiments. For example, the processor 620 may include multiple microprocessors that are configured to independently execute the methods described herein or are configured to perform steps or subroutines of the methods described herein such that the multiple processors cooperate to achieve the functionality described herein. Further, where the device 600 is implemented in a cloud computing system, the various hardware components may belong to separate physical systems. For example, the processor 620 may include a first processor in a first server and a second processor in a second server.

Figure 7:
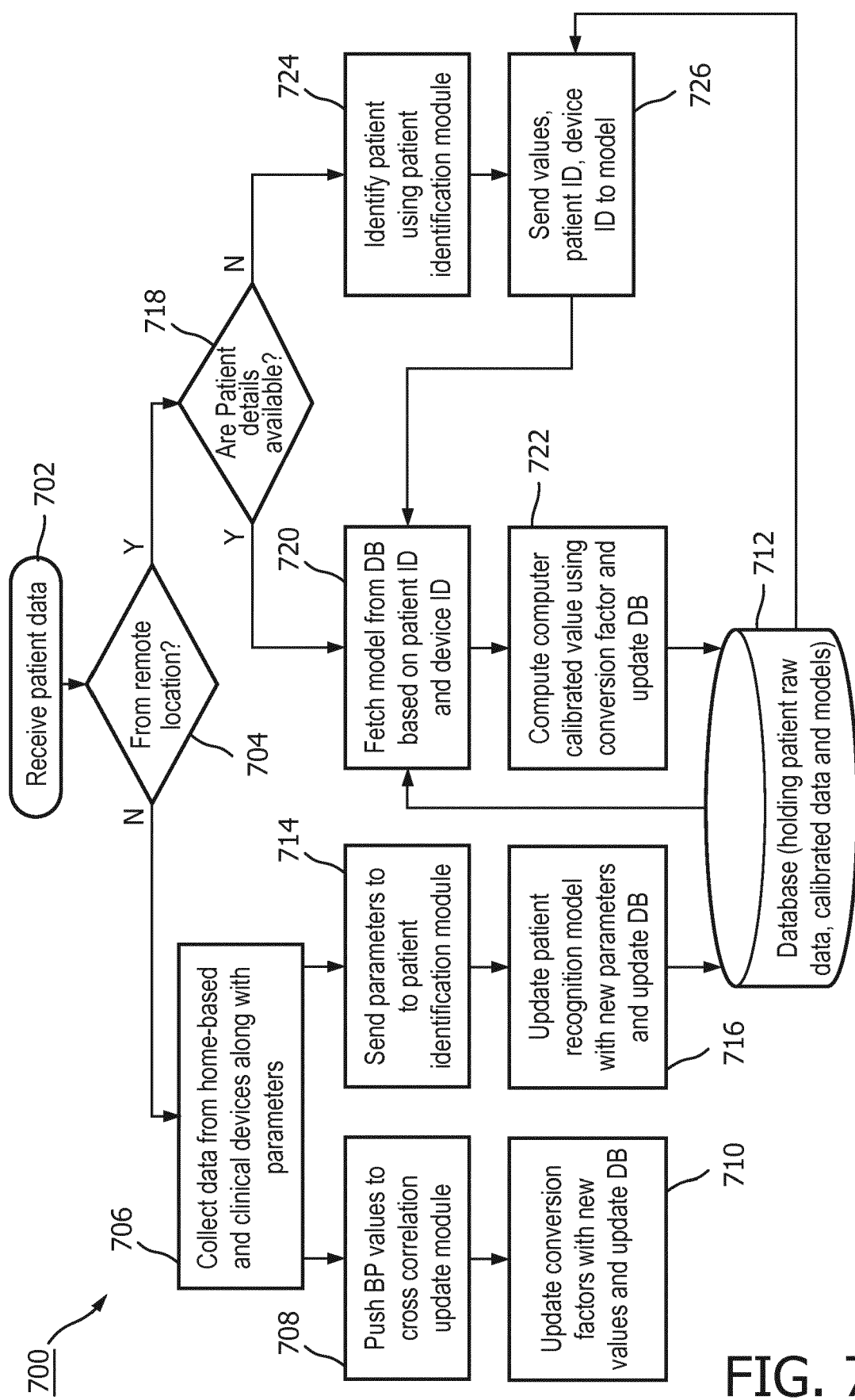
FIG. 7 is a block diagram illustrating a further example of a method of calibrating a medical monitoring device according to a further embodiment.

FIG. 7 shows an example method of calibrating physiological measurements from a medical monitoring device that can be executed using an apparatus such as the apparatus 600 described in FIG. 6 above.

In a first block 702, patient data is received, for example by a network interface such as the network interface 650. In this context, patient data may refer to physiological measurements that are to be calibrated or parameter data relating to the user, or the medical monitoring device used to make the physiological measurement. Examples of parameter data are provided in the previous examples above.

At 704, it is determined whether the received data is from a remote location. If the data is received from a remote location, then this implies that the patient data has been received from a home based device, whereas if the data is not from a remote location, then this implies that the data is from a clinical setting and that there is an opportunity to update the calibration model of an associated home based device. In 704, if it is determined that the data is not from a remote location (e.g. likely clinical data), then the received patient data is collected alongside data from a home based device in 706. The clinical and home based measurements are used to update the cross correlation in 708 and the conversion factor in 710 in a cross correlation update module such as cross correlation update module 664 and conversion factor calculation module such as conversion factor calculation module 665 respectively. The received data, in addition to the updated cross correlation and conversion factors are then pushed to a database, such as database 666, in step 712.

Parameters relating to the measurement(s), the clinical device and/or the home device are used in step 714 to improve models generated by an AI based engine such as AI based engine 662 to match measurements to a user. The models generated by AI based engines are referred to in this example as patient recognition models. Once the patient recognition models are updated by AI based engine 662, they are sent to a database such as database 666 in step 712.

Returning now to step 704, if it is determined that the measurement is from a remote location, then the method proceeds to match the patient data to an individual. In step 718, it is determined whether patient details are available for the measurement. If patient details are available, then the method proceeds to step 720 where an appropriate conversion factor is fetched from a database such as database 666, for the identified patient using the identified device. In step 722, the conversion factor is used to calibrate the received measurement and in 712, a database such as database 666 is updated with the newly calibrated measurement.

If in step 718 it is determined that patient details are not available, then the method proceeds to step 724 where the patient data is sent to a patient identification module, such as patient identification module 663. In step 726, the patient identification module uses the available data and the patient recognition model generated by an AI based engine such as AI based engine 662 to identify the patient.

Once the patient is identified, then the method proceeds to step 720, where a conversion factor appropriate for the identified patient is retrieved from a database such as database 666 and used in step 722 to calibrate the patient data.

In this way, new data is used efficiently, to improve the calibration process and patient identification models wherever possible.

Variations to the disclosed embodiments can be understood and effected by those skilled in the art in practicing the principles and systems disclosed herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A method of calibrating measurements made using a first medical monitoring device, the method comprising:
   obtaining a first conversion factor comprising a first cross correlation that describes the correlation between measurements made using the first medical monitoring device and measurements made using a second medical monitoring device;
   obtaining a calibration factor for the user, wherein the calibration factor indicates whether the physiological measurement should be divided or multiplied by the first conversion factor;
   using the first conversion factor to convert measurements from the first medical monitoring device onto the same scale as measurements from the second medical monitoring device;
   receiving a first set of measurements from the first medical monitoring device;
   receiving a second set of measurements from the second medical monitoring device; and
   computing the first cross correlation as the cross correlation between the first set of measurements and the second set of measurements; and
   generating the first conversion factor from the first cross correlation by scaling the first cross correlation using a scaling factor, wherein the scaling factor comprises one or more parameters relating to at least one of the first medical monitoring device and the second medical monitoring device.

2. The method as in claim 1, wherein the one or more parameters relate to the degradation in performance over time of at least one of the first medical monitoring device and the second medical monitoring device.

3. The method as in claim 2, wherein the degradation in performance is described by an exponential term and generating the first conversion factor further comprises:
   adding the exponential term to the first cross correlation.

4. The method as in claim 3, wherein the first conversion factor, C, is given by:

$$C = \sqrt{\frac{P_{xy}^2}{P_{xx}P_{yy}}} + e^{-\omega t};$$

wherein $P_{xy}=\Sigma xy-n\overline{x}\overline{y}$ represents the correlation between the measurements, x, from the first medical monitoring device and the measurements, y, from the second medical monitoring device; $P_{xx}=\Sigma(x_i-\overline{x})^2$ represents the auto-correlation of the measurements of the first medical monitoring device; $P_{yy}=\Sigma(y_i-\overline{y})^2$ represents the auto-correlation between the measurements from the second medical monitoring device; and $e^{-\omega t}$ represents the device performance degradation of the first medical monitoring device.

5. The method as in claim 1, wherein the method further comprises:
  receiving a third set of measurements from the first medical monitoring device;
  receiving a fourth set of measurements from the second medical monitoring device; and
  updating the first conversion factor using the received third and fourth sets of measurements.

6. The method as in claim 1, further comprising:
  receiving a fifth set of measurements from the first medical monitoring device;
  receiving a sixth set of measurements from a third medical monitoring device;
  computing a second cross correlation between the fifth set of measurements and the sixth set of measurements; and
  generating a second conversion factor using the first and second cross correlations to convert measurements from the third medical monitoring device onto the same scale as measurements from the second medical monitoring device.

7. The method as in claim 6, wherein generating the second conversion factor further comprises:
  calculating an intermediate conversion factor using the second cross correlation to convert measurements from the third medical monitoring device onto the same scale as the first medical monitoring device; and
  multiplying the intermediate conversion factor by the first conversion factor to obtain the second conversion factor.

8. The method as in claim 1, wherein using the first conversion factor further comprises:
  dividing the physiological measurement by the first conversion factor after the calibration factor indicates that the physiological measurement should be divided by the conversion factor; and
  multiplying the physiological measurement by the conversion factor after the calibration factor indicates that the physiological measurement should be multiplied by the conversion factor.

9. The method as in claim 8, wherein the calibration factor is given by:

factor=1×sign($\Sigma(x-y)$), wherein x and y are pairs of contemporaneous measurements of the first and second devices respectively.

10. The method as in claim 1 wherein the first and second sets of measurements are taken contemporaneously.

11. The method as in claim 1, wherein the first medical monitoring device is a home-based medical monitoring device and the second medical monitoring device is a clinical device.

12. A medical monitoring device comprising a computer processor configured to:
  obtain a first conversion factor comprising a first cross correlation that describes the correlation between measurements made using the medical monitoring device and measurements made using a second medical monitoring device;
  obtain a calibration factor for the user, wherein the calibration factor indicates whether the physiological measurement should be divided or multiplied by the first conversion factor;
  use the first conversion factor to convert measurements from the medical monitoring device onto the same scale as measurements from the second medical monitoring device;
  receive a first set of measurements from the medical monitoring device;
  receive a second set of measurements from the second medical monitoring device; and
  compute the first cross correlation as the cross correlation between the first set of measurements and the second set of measurements;
  generate the first conversion factor from the first cross correlation by scaling the first cross correlation using a scaling factor, wherein the scaling factor comprises one or more parameters relating to at least one of the medical monitoring device and the second medical monitoring device.

13. A non-transitory computer readable medium having computer readable code embodied therein, the computer readable code being configured such that, on execution by a suitable computer or processor, the computer or processor is caused to perform a method of calibrating measurements, the non-transitory computer readable medium comprising:
  instructions for obtaining a first conversion factor comprising a first cross correlation that describes the correlation between measurements made using a first medical monitoring device and measurements made using a second medical monitoring device;
  instructions for obtaining a calibration factor for the user, wherein the calibration factor indicates whether the physiological measurement should be divided or multiplied by the first conversion factor;
  instructions for using the first conversion factor to convert measurements from the first medical monitoring device onto the same scale as measurements from the second medical monitoring device;
  instructions for receiving a first set of measurements from the first medical monitoring device;
  instructions for receiving a second set of measurements from the second medical monitoring device;
  instructions for computing the first cross correlation as the cross correlation between the first set of measurements and the second set of measurements; and
  instructions for generating the first conversion factor from the first cross correlation by scaling the first cross correlation using a scaling factor, wherein the scaling factor comprises one or more parameters relating to at least one of the first medical monitoring device and the second medical monitoring device.

14. The method as in claim 1, wherein the one or more parameters relate to one or more properties of the medical monitoring device, the one or more properties comprising an identification number, a device model, a tolerance limit, an operating environment, an accuracy, a performance of the medical monitoring device.

* * * * *